US005688517A

United States Patent [19]

Helson et al.

[11] Patent Number: 5,688,517

[45] Date of Patent: Nov. 18, 1997

[54] METHOD FOR ASSESSING SENSITIVITY OF TUMOR CELLS TO CEPHALOMANNINE AND 10-DEACETYLTAXOL

[75] Inventors: Lawrence Helson, Chappaqua, N.Y.; Sterling K. Ainsworth, Boulder, Colo.

[73] Assignee: NaPro BioTherapeutics, Inc., Boulder, Colo.

[21] Appl. No.: 10,821

[22] Filed: Jan. 29, 1993

[51] Int. Cl.$^6$ .................................................. A61F 13/00
[52] U.S. Cl. ........................ 424/422; 424/400; 424/449; 424/450; 436/63; 436/64; 436/815; 514/772.3
[58] Field of Search ........................ 436/63, 64, 815; 424/422, 400, 449, 450; 514/772.3

[56] References Cited

U.S. PATENT DOCUMENTS

| | | | |
|---|---|---|---|
| 4,206,221 | 6/1980 | Miller et al. | 424/278 |
| 4,814,470 | 3/1989 | Colin et al. | 514/449 |
| 4,857,653 | 8/1989 | Colin et al. | 549/511 |
| 4,924,011 | 5/1990 | Denis et al. | 549/510 |
| 4,924,012 | 5/1990 | Colin et al. | 549/510 |
| 5,254,580 | 10/1993 | Chen | 514/449 |

FOREIGN PATENT DOCUMENTS

| | | |
|---|---|---|
| 0253738 | 7/1987 | European Pat. Off. . |
| 0253739 | 7/1987 | European Pat. Off. . |
| 0336840 | 5/1989 | European Pat. Off. . |
| 0336841 | 5/1989 | European Pat. Off. . |

OTHER PUBLICATIONS

Scudiero et al Cancer Research 48, 4827–4833, 1981.
The Chemistry of Taxol, a Clinically Useful Anticancer Agent, *Journal of Natural Products*, vol. 53, No. 1, pp. 1–12, Jan.–Feb. 1990 by Kingston et al.
Wani, M.C., Taylor, H.L., Wall, M.E., Coggon, P. and McPhail, A.T. Journal of American Chemical Society, 93, 2325 (1971).
Powell, R.G., Miller, R.W. and Smith Jr., C.R., J.C.S. Chem. Comm. 102 (1979).
McLaughlin, J.L., Miler, R.W., Powell, R.G. and Smith Jr. C.R., Journal of Natural Products 44, 312 (1981).
Miller, R.W., Powell, R.G. and Smith Jr., C.R., Org. Chem., 46, 1469 (1981).
Senilh, V., Blechert, S., Colin, M., Guenard, D., Picot, F., Potier, P. and Varenne, P., Journal of Natural Products 47, 131 (1984).
Mellado, W., Magri, J.F., Kingston, D.G.I., Garcia–Arenas, R., Orr, G.A. and Horowitz, S.B., Biochemical and Biophysical Research Communications, 124, 329 (1984).
Satish, A.V., Dissertation Abstracts Interntl, 48, 1052–B (1987). Voegelein, F.G., Guenard, D. and Potier, P., Journal of Natural Products, 50 9 (1987).
Parness, J., Kingston, D.G.I., Powell, R.G., Harracksingh, C. and Horwitz, S.B., Biochemical and Biophysical Research Communications, 105, 1082 (1982).

*Primary Examiner*—D. Gabrielle Phelan
*Attorney, Agent, or Firm*—Timothy J. Martin

[57] ABSTRACT

A method for assessing the sensitivity of a patient's tumor cells to cephalomannine and 10-deacetyltaxol in order to treat those tumor cells involves the removal of a sample of the tumor cells and establishing a cell line therefrom. Cells from the cell line are cultured and then contacted with varying concentrations of cephalomannine or 10-deacetyltaxol to form treated cells. The treated cells are assessed to determine the cytotoxic effect of the cephalomannine and/or the 10-deacetyltaxol and, where cytotoxic response is exhibited, a therapeutic dosage is formulated using the selected concentration of cephalomannine or 10-deacetyltaxol and a carrier material. The method is particularly useful for neural and glial tumor cells.

15 Claims, No Drawings

METHOD FOR ASSESSING SENSITIVITY OF TUMOR CELLS TO CEPHALOMANNINE AND 10-DEACETYLTAXOL

FIELD OF INVENTION

The present invention is related to the use of certain diterpenes (that are not taxol) as antitumor agents. More specifically, the present invention relates to the drugs, 10-deacetyltaxol and cephalomannine and their antineoplastic activities against cancerous cells.

BACKGROUND

Taxol isolated from the bark of the Western yew, "Taxus brevifolia", is a complex diterpene. During isolation of taxol from plant material, members of other taxanes have been collected and identified. Examples of these taxanes include 10-deacetyltaxol, baccatin III, 10-deacetylbaccatin III, and cephalomannine. Unfortunately, numerous studies indicate that taxol is highly cytotoxic, and the other taxanes such as 10-deacetyltaxol, cephalomannine, 10-deacetylbaccatin III and baccatin III have less cytotoxic effects than taxol. Although U.S. Pat. No. 4,206,221 reports that cephalomannine had significant cytotoxic effective against leukemia cells of the strain P388. The industry has focused of research and development taxol and has virtually ignored the other taxanes.

Taxol's and presumably other taxane derivatives mechanism of action is based on taxol's unique capacity to stabilize microtubulin assembly which leads to microtubule bundling and abnormal spindle aster formation. Once microtubules are stabilized, the cells lose their capacity to undergo dynamic reorganization of their microtubular network and normal mitoses. These changes impact upon mitogenic signaling from the membrane, intracellular transport of metobolites, and ordered movement of chromosomes associated with cell proliferation; all of which lead to cell death.

The use of 10-deacetyltaxol and cephalomannine as agents having antineoplastic properties has been discounted by the industry because of taxol's superior cytotoxic effect. However, taxol has certain draw-backs not associated with cephalomannine and 10-deacetyltaxol. Taxol is insoluble in water. Thus, to have clinical usefulness taxol must be placed in a carriers such as a polyoxyethylated castor oil (cremophår).

Taxol shows some toxic effects, but severe allergic reactions have resulted from carriers administered in conjunction with taxol to compensate for taxol's low water solubility. To solve taxol's water solubility problems the industry has attempted to create water soluble derivatives of taxol. The industry has ignored the taxanes such as 10-deacetyltaxol and cephalomannine which are significantly more water soluble then taxol because of their slightly lower cytotoxicity. Surprisingly the present invention evidences that 10-deacetyltaxol and cephalomannine showed 91% and 94.6% cell kill respectively on certain cell lines while taxol evidenced 94.3% cell kill at the same concentration and exposure time. Plus the carriers necessary for administration of 10-deacetyltaxol and cephalomannine in vivos cause less severe allergic reactions because the carriers are not formulated to compensate for material that is totally insoluble in $H_2O$.

There remains a need for antineoplastic agents which achieve high levels of cell kill but are more water soluble then taxol. 10-deacetyltaxol and cephalomannine of the present invention are significantly more water soluble then taxol. Many of the limitations presented by taxol are greatly reduced by using 10-deacetyltaxol and cephalomannine.

SUMMARY OF THE INVENTION

An object of the present invention is to provide as drugs, taxanes, which are more water soluble then taxol and which have significant antineoplastic properties.

Another object of the present invention is to provide transdermal patches for having cephalomannine or 10-deacetyltaxol as a drug application to melanoma and to systemic delivery.

Still a further object of the present invention is to provide a method of testing the cytotoxicity effects of the present invention on a patient's tumor cell prior to patient treatment.

Still a further object of the present invention is to provide a method of determining the optimal drug scheduling and dosing for treatment of a patient's tumor.

Yet another object of the present invention is to provide a systemic treatment of neural tumors.

One form of the present invention provides a method for assessing the sensitivity of a patient's tumor cells to cephalomannine and 10-deacetyltaxol prior to selecting cephalomannine or 10-deacetyltaxol as a method of treating the tumor cells. The method comprises the following steps removing from the patient, a sample of tumor cells, establishing tumor cell line culturing the tumor cells in a medium, contacting selected concentrations of cephalomannine and/ or 10-deacetyltaxol with the cultured tumor cells whereby forming treated cells and performing an assay on the treated cells to assess viability of the cells to cephalomannine and 10-deacetyltaxol and selecting concentrations of cephalomannine and 10-deacetyltaxol for in vivos application based on the viability of the cells. The method also can including the step of incubating the cells in the medium in 5% $CO_2$ in air. And the step of solubilizing the cells in alcohol. The tumor cells can be neural tumor cells. The assay for assessing the viability of the tumor cells is preferably the MTT assay. However other procedures for analysizing the viability of the tumor cells can be employed.

The present invention also teaches a method of treating malignancy by a transdermal patch adapted to be placed on the skin of a patient. This treatment method comprising the steps of preparing a formulation containing a carrier material and at least one of the drugs cephalomannine and 10-deacetyltaxol in therapeutic amounts, contacting the formulation with the transdermal patch to form a drug supplying transdermal patch, and next applying said drug supplying transdermal patch to the skin of the patient having the malignancy. The preferred type of malignancy for this method is melanoma but other malignancies can be treated in this manner. The carrier material can be polyethylene glycol, a cyclodextrine, or liposomes.

In its broadest form the present invention teaches a method of treating a patient's malignancy with a nontaxol taxane. The method includes the steps of assaying the malignancy with at least one nontaxol taxane, which is formed by nature, to determine the sensitivity of the malignancy to the taxane. The next step is treating the malignancy with a therapeutic amount of the taxane whereby the malignancy is subjected to the cytotoxic effect of said taxane. The preferred nontaxol taxane is 10-deacetyltaxol or cephalomannine.

This method more specifically includes the step of preparing a formulation of the nontaxol taxane, which is formed by nature, with a pH adjusted polyoxyethylated castor oil. This formulation can be intravenously administered to the patient having the malignancy. The present invention is applicable to nonhuman patient's and human patients.

DETAILED DESCRIPTION

The following compounds, 10-deacetyltaxol, 10-deacetylbaccatin III, baccatin III and cephalomannine were tested for in vitro activity against two glioblastoma multiform (Sample 1 and 2) and two neuroblastoma (Sample 3 and 4) cell lines and the compounds activity was compared with that of taxol. 10-deacetyltaxol and cephalomannine were found to have significant cytotoxic effects on neural tumors. Cephalomannine, 10-deacetyltaxol have cytotoxic effects that are therapeutically useful.

CELL CULTURE

All human cell lines except Sample 4 (which was obtained from the American Type Culture collection, 12301 Park Lawn Drive, Rockville, Md.), were established and cultured as described in L., Helson C.: Establishment of a new cell line, VA-N-BR, from a primitive neuroblastoma tumor of the abdomen; Anticancer Research 12:467–472, 1992. Different methods of culturing the human cell lines are known to those of skill in the art. The method of establishing a cell line for stock cells is listed a an example and is not intended to limit the scope of the present invention.

This is a specific example of establishing a cell line from which stock cells were generated from a neuroblastoma originating in the abdomen of a six year old male. One small serosal tumor specimen was extracted in surgery from the patient and was minced and suspended in Eagle's™ (commercially available) minimal essential medium supplemented by 15% heat activated fetal bovine serum and incubated at 37° C. in a humidified atmosphere of 5% carbon dioxide in air.

TUMOR CELL CULTURE

On the seventh day of incubation the flasks contained small round highly refractile tumor cells layered out upon and between attached fibroblasts. The cultured medium was supplemented every four to six days for three weeks. After three weeks the monolayer of tumor cells and fibroblasts were harvested with trypsin 0.25% —EDTA 0.1% and placed in fresh medium. By the thirteenth week the the tumor cells grew in the absence of fibroblasts. Tumor cells were harvested with trypsin, EDTA and the stock cells were seeded in microwells.

CYTOTOXICITY ASSAYS

The cytotoxic effects of taxol, 10-deacetyltaxol, cephalomannine, baccatin III and 10-deacetylbaccatin III were determined in tumor cells growing as attached monolayers. Stock cells in 25 cm$^2$ flasks were incubated in medium (Dubelccos Modified Eagles's Medium and 10% fetal bovine serum) at 37° C. in 5% $CO_2$ in air for five days. The medium specified is listed as an example and is not intended to limit the scope of the invention. Various mediums can be employed. Medium was renewed on the sixth day and on the seventh day the cells were detached into a single cell suspension with trypsin/EDTA, counted, and aliquots plated at 3,000–5,000 cells in 0.1 ml fresh media in each well of a 96 well microtiter plate (Becton-Dickinson Labware, 2 Bridewate Lane, Lincoln Park, N.J.). Within 24 hours the cells formed attached monolayers. Research grade taxol was obtained from three sources: Cal Biotech, Inc., La Jolla, Calif. from the National Cancer Institute, and from NaPro BioTherapeutics, Boulder, Colo. as a 99.2% purified product. The taxol from NaPro was compared with taxol supplied by the NCI using HPLC. Cephalomannine was obtained as an 87% purified product containing 1.4% taxol. The cephalomannine did not contain any 10-deacetyltaxol. 10-deacetyltaxol was obtained as an 80% purified product and contained 4.5% taxol. The 10-deacetyltaxol did not contain any cephalomannine. Baccatin III was obtained as a 95% purified product. 10-deacetylbaccatin III was obtained as a 95% purified product. These taxanes were obtained from NaPro BioTherapeutics, Inc., Boulder, Colo. All compounds were solubilized in 95% alcohol to 100 µg/ml. Then the compounds were further diluted with complete media to 0.2–20 µg/ml. Various concentrations of freshly diluted taxanes were added to replicate wells in 0.1 ml volumes. After one hour or 24 hours depending on the length of the experiment at 37° C. the media was aspirated and replaced by drug free media in both treated and control wells.

CELL VIABILITY (MTT).

Viability of the cell lines five days after exposure to drugs was determined by the MTT assay following published procedures Carmichael J., DeGraff WG, Gazdor AP et al: Evaluation of tetrazolium-based semi-automated colormetric assay: Assessment of chemosensitivity testing. Cancer Research 47:936–942, 1987. Six replicate wells for control and for each test concentration were used in every experiment. Each experiment was done three separate times. The MTT, 3-(4,5-dimethythiazol-2-yl)-2,5-diphenyl-tetrazolium bromide (thiazolyl blue), assay depends on the cellular reduction of MTT by viable cells to a blue formazan product which is then measured spectrophometrically. (This is commercially available from Signa Chemical Company, St. Louis, Mo.) 0.1 mgr# (50 µl of 2# mg/ml) of MTT was added to each well and incubated at 37° C. for 4 hours. The plates of wells were then flipped to remove excess material and DMSO (dimethyl sulfoxide) was added to solubilize the formazancrystals and the plates were shaken on a rotary shaker for 10 minutes. The plates were then read for absorbance with a scanning multiwell spectrophotometer (ELISA Reader, Botek Instruments) at a wavelength of 570 nm. The following data resulted.

TABLE I

Toxicity as percent control

| * | ug/ml | A 1h | A 24h | B 1h | B 24h | C 1h | C 24h |
| --- | --- | --- | --- | --- | --- | --- | --- |
| 3 | 0.1 | 73 | 84 | 37 | 75 | 35 | 71 |
|   | 1.0 | 90 | 92 | 85 | 88 | 76 | 88 |
|   | 10.0 | 94.3 | 94.5 | 94.6 | 92.3 | 91 | 93 |
| 4 | 0.1 | 14 | 0 | 0 | 0 | 0 | 0 |
|   | 1.0 | 53 | 51 | 0 | 8 | 0 | 9 |
|   | 10.0 | 76 | 57 | 0 | 52 | 0 | 38 |
| 1 | 0.1 | 11 | 4 | 0 | 0 | 0 | 0 |
|   | 1.0 | 45 | 33 | 20 | 24 | 41 | 22 |
|   | 10.0 | 54 | 33 | 70 | 54 | 64 | 41 |
| 2 | 0.1 | 57 | 66 | 38 | 59 | 39 | 61 |
|   | 1.0 | 75 | 27 | 62 | 65 | 64 | 69 |
|   | 10.0 | 74 | 76 | 76 | 78 | 73 | 73 |

A. Taxol
B. Cephalomannine
C. 10-deacetyltaxol
*Sample

Chromatographic and other chemicals analysis revealed the NCI taxol was essentially identical to the product from NaPro BioTherapeutics, Inc., hence, no cytotoxicity studies were performed with the NCI material. Concentration of 0.1 µg/ml to 10.0 µg/ml taxol for 1 or 24 hours caused a range of dose related toxicities which were consistent over three separate experiments (Table I). Depending on the concentration and cell line a range of 0% to 94.6% cell kill was observed. Sample 3 was consistently the most sensitive, and Sample 4 the most resistant cell line (Table I). Baccatin III and 10-deacetylbaccatin III were not toxic. Both cephalomannine and 10-deacetyltaxol were 33–53% less cytotoxic than taxol at equal concentrations and exposure durations. The order of sensitivity to the three drugs exhibited in four cell lines remained consistent and independent of the duration of exposure within the concentrations used.

DISCUSSION

These experiments offer the first evidence that taxol, cephalomannine, and 10-deacetyltaxol cause cytopathic effects in cultured human and neural tumor cell lines. It is not surprising that clinical neuropathy following taxol has been reported, since interference with microtubular assembly can impact upon transport of trophic substances such as nerve growth factor, which is normally transported via the microtubular network and ultimately nerve function.

The cytotoxic profile of 10-deacetyltaxol is different from taxol since it is more polar and water soluble. Clinical use of these drugs in patient or animals with central and peripheral nerve tumors through systemic application or intravenous application would result in cytotoxic effects with less side effects associated with taxol's water insolubility. 10-deacetyltaxol's use in highly malignant glial tumors characterized by neovascularization and enhanced drug permeability should not be an obstacle except possibly for drug penetration to disseminated tumor cells in the brain which are protected by the blood brain barrier. This phenomenon may somewhat limit tumor cell eradication in some patients.

These in vitro data indicate taxol, cephalomannine, and 10-deacetyltaxol can affect survival of peripheral neuroblastoma and central malignant glioma tumor cell lines. The refractory neuroblastoma cell line of Sample 4 and the very sensitive Sample 3 cell line were obtained from bone marrow metastases of heavily pre-treated patients. The Sample 4 cell line expresses 10-fold greater drug resistance than the Sample 3 cell line. Most probably this is due to its high expression of Multiple Drug Resistance (MDR) 1 since the specific target determining susceptibility to taxol is the microtubule, and the drug must reach this target in sufficient amounts to initiate cytopathic changes. Other determinants of taxol resistance such as differences in drug microtubule reactions may not be required to explain this difference.

In conclusion, unexpectedly, cephalomannine, and 10-deacetyltaxol exert considerable cytotoxic effects on neuroblastoma and glial tumors. These two compounds appear to be slightly less cytotoxic than taxol, hence they may in certain instances demand higher concentrations to equal taxol's effect on tumored tissues; however, they often offer a better toxicity profile in the clinical setting.

The following method can be employed to determine the toxicity profile of the selected compound to the patient's malignancy. First as noted above, the patient's tumor cells should be established and the cephalomannine and 10-deacetyltaxol should be contacted with the cultured cells. Next the MTT assay should be run and analyzed to determine the sensitivity of the tumor cells to the drug. This data should be used to determine appropriate patient dosages of the selected drug. The exposure duration of the drug to the cells can be varied to determine the appropriate scheduling of the dosages to the patient. When the drug is used in vivos the patient should be closely monitored to determine if there are any allergic reactions to the drugs.

Cephalomannine and 10-deacetyltaxol exhibit more water solubility then does taxol. Therefore some of the carrier materials which maybe highly successful for administration of cephalomannine and 10-deacetyltaxol can be selected to avoid inducing acute hypersensitivity reactions. Carrier materials such as polyethylene glycol (PEG), cyclodextrine and liposomes are candidates for a injection carrier for a cephalomannine or a 10-deacetyltaxol formulation. Likewise, cremophar can also be employed although it often limits the clinical usefulness of the drug. PEG, cyclodextrines and liposomes maybe especially useful as carrier material in cephalomannine and 10-deacetyltaxol formulation which are applied by a transdermal patch to a patient having a malignancy. A patch maybe used for systemic administration of cephalomannine and 10- deacetyltaxol or alternatively it may be placed directly on the malignancy. By way of example direct skin patch application to the tumor may be a successful method of treating melanoma.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. The method for assessing the sensitivity of a patient's tumor cells to cephalomannine and 10-deacetyltaxol prior to selecting cephalomannine or 10-deacetyltaxol as a method of treating said tumor cells, said method comprising the following:

removing a sample of tumor cells from the patient;

establishing a cell line from said sample;

culturing cells from said cell line in a medium;

contacting selected varying concentrations of at lest one compound selected from the group consisting of cephalomannine and 10-deacetyltaxol with at least some of said cultured tumor cells, thereby to form treated cells;

performing an assay on said treated cells to assess cytotoxic effect on said treated cells by cephalomannine and 10-deacetyltaxol; and in instances where said cells exhibit a cytotoxic response to said compound, thereafter formulating a therapeutic dosage containing a carrier material and a selected concentration of said compound for in vivos injection, said concentration determined by the cytotoxic effect the treated cells to said compound in said assay.

2. A method according to claim 1 wherein said tumor cells are neural tumor cells.

3. A method according to claim 1 wherein said assay is the MTT assay.

4. A method according to claim 1 wherein said medium includes 10% fetal bovine serum.

5. A method according to claim 1 including the step of incubating said cells in said medium in 5% $CO_2$ in air.

6. A method according to claim 5 including the step of detaching said cells in said medium in 5% $CO_2$ in air into a single cell suspension with trypsin/EDTA.

7. A method according to claim 6 wherein the cells are solubilized in alcohol.

8. The method for assessing the sensitivity of a patient's neural and glial tumor cells to cephalomannine or 10-deacetyltaxol as a method of treating said tumor cells, said method comprising the following steps:

removing a sample of the tumor cells from the patient;

establishing a cell line from said sample;

culturing cells from said cell line in a medium;

contacting selected varying concentrations of at lest one compound selected from the group consisting of cephalomannine and 10-deacetyltaxol with at least some of said cultured tumor cells thereby to form treated cells;

performing an assay on said treated cells to assess cytotoxic effect on said treated cells by varying concentrations of said compound; and in instances where said cells exhibit a cytotoxic response to said compound, thereafter formulating a therapeutic dosage containing a carrier material and a selected concentration of said compound for in vivos injection, said concentration determined by the cytotoxic response of the treated cells to the selected concentration of said compound in said assay.

9. A method according to claim 8 wherein said assay is the MTT assay.

10. A method according to claim 8 wherein said medium includes 10% fetal bovine serum.

11. A method according to claim 8 including the step of incubating said cells in said medium in 5% $CO_2$ in air.

12. A method according to claim 11 wherein said incubation period is about five days.

13. A method according to claim 11 including the step of detaching said cells in said medium in 5% $CO_2$ in air into a single cell suspension with trypsin/EDTA.

14. A method according to claim 12 wherein the cells are solubilized in alcohol.

15. The method for assessing the sensitivity of a patient's tumor cells to cephalomannine and 10-deacetyltaxol prior to selecting cephalomannine or 10-deacetyltaxol as a method of treating said tumor cells, said method comprising the following steps:

removing a sample of tumor cells from the patient;

establishing a cell line from said sample;

culturing cells from said cell line in a medium;

contacting selected varying concentrations of at least one compound selected from the group consisting of cephalomannine and 10-deacetyltaxol with at last some of said cultured tumor cells thereby to form treated cells; and performing an assay on said treated cells to assess cytotoxic response of said treated cells to the varying concentrations of said compound to establish an appropriate dosage sufficient to have a cytotoxic effect on said cultured tumor cells where said treated cells exhibited said cytotoxic response.

* * * * *